(12) United States Patent
Lee et al.

(10) Patent No.: US 12,239,807 B2
(45) Date of Patent: Mar. 4, 2025

(54) INTRAVESICAL DRUG DELIVERY DEVICES AND METHODS INCLUDING ELASTIC POLYMER-DRUG MATRIX SYSTEMS

(71) Applicant: TARIS Biomedical LLC, Lexington, MA (US)

(72) Inventors: Heejin Lee, Bedford, MA (US); Karen Daniel, Newton, MA (US)

(73) Assignee: TARIS Biomedical LLC, Lexington, MA (US)

( * ) Notice: Subject to any disclaimer, the term of this patent is extended or adjusted under 35 U.S.C. 154(b) by 686 days.

(21) Appl. No.: 16/989,208

(22) Filed: Aug. 10, 2020

(65) Prior Publication Data

US 2020/0368508 A1    Nov. 26, 2020

Related U.S. Application Data

(62) Division of application No. 15/321,110, filed as application No. PCT/US2015/037887 on Jun. 26, 2015, now Pat. No. 10,737,078.

(Continued)

(51) Int. Cl.
*A61M 31/00* (2006.01)
*A61K 9/00* (2006.01)
*A61M 25/00* (2006.01)

(52) U.S. Cl.
CPC ......... *A61M 31/002* (2013.01); *A61K 9/0034* (2013.01); *A61M 25/0009* (2013.01);
(Continued)

(58) Field of Classification Search
CPC ............ A61M 31/002; A61M 25/0009; A61M 2205/0216; A61M 2207/00; A61M 2210/1085; A61K 9/0034
See application file for complete search history.

(56) References Cited

U.S. PATENT DOCUMENTS 3,854,480 A * 12/1974 Zaffaroni ............. A61K 9/7007
424/435
4,871,542 A    10/1989 Vilhardt
(Continued)

FOREIGN PATENT DOCUMENTS

| WO | 2012/048104 A1 | 4/2012 |
|---|---|---|
| WO | 2013/177068 A1 | 11/2013 |
| WO | 2015/175538 A1 | 11/2015 |

OTHER PUBLICATIONS

International Search Report and Written Opinion in Corresponding PCT application PCT/US2015/037887, mailed Nov. 26, 2015.
(Continued)

*Primary Examiner* — James D Ponton
(74) *Attorney, Agent, or Firm* — Eversheds Sutherland (US) LLP

(57) ABSTRACT

Intravesical drug delivery devices are provided which may include an elongated body formed of a matrix system of a drug dispersed in a silicone, wherein the elongated body has a first end, an opposed second end, and an intermediate portion between the first and second ends, and wherein the silicone of the matrix system is cured to bias the elongated body in a coiled retention shape, such that the device is elastically deformable between a relatively straightened shape suited for insertion of the device through a urethra and into the urinary bladder of a patient and the coiled retention shape which is suited to retain the device within the urinary bladder.

14 Claims, 6 Drawing Sheets

Related U.S. Application Data

(60) Provisional application No. 62/017,775, filed on Jun. 26, 2014.

(52) U.S. Cl.
CPC . *A61M 2205/0216* (2013.01); *A61M 2207/00* (2013.01); *A61M 2210/1085* (2013.01)

(56) References Cited

U.S. PATENT DOCUMENTS

| | | | |
|---|---|---|---|
| 5,062,829 A * | 11/1991 | Pryor | A61D 7/00 604/890.1 |
| 5,694,947 A | 12/1997 | Lehtinen | |
| 6,039,967 A | 3/2000 | Ottoboni et al. | |
| 6,183,461 B1 | 2/2001 | Matsuura et al. | |
| 6,524,608 B2 | 2/2003 | Ottoboni et al. | |
| 7,077,859 B2 | 7/2006 | Sirhan et al. | |
| 7,288,084 B2 | 10/2007 | Li | |
| 8,343,516 B2 | 1/2013 | Daniel et al. | |
| 8,679,094 B2 | 3/2014 | Cima et al. | |
| 8,690,840 B2 | 4/2014 | Lee et al. | |
| 8,801,694 B2 | 8/2014 | Lee et al. | |
| 9,017,312 B2 | 4/2015 | Lee et al. | |
| 9,107,816 B2 | 8/2015 | Lee et al. | |
| 9,283,361 B2 | 3/2016 | DiCesare et al. | |
| 9,586,035 B2 | 3/2017 | Cima et al. | |
| 2004/0022824 A1 * | 2/2004 | Li | A61L 31/148 604/500 |
| 2004/0122507 A1 | 6/2004 | Henderson | |
| 2006/0025726 A1 * | 2/2006 | Fischer, Jr. | A61M 25/0017 424/422 |
| 2006/0052757 A1 | 3/2006 | Fischer et al. | |
| 2006/0105010 A1 | 5/2006 | Rahe et al. | |
| 2006/0122689 A1 | 6/2006 | Kocur et al. | |
| 2007/0161968 A1 | 7/2007 | Fischer, Jr. | |
| 2009/0149833 A1 * | 6/2009 | Cima | A61M 25/0108 604/93.01 |
| 2010/0331770 A1 | 12/2010 | Lee et al. | |
| 2011/0060309 A1 | 3/2011 | Lee | |
| 2012/0089121 A1 | 4/2012 | Lee | |
| 2012/0089122 A1 * | 4/2012 | Lee | A61L 29/16 604/517 |
| 2012/0107385 A1 | 5/2012 | Mahashabde et al. | |
| 2012/0203203 A1 * | 8/2012 | Lee | A61K 31/337 604/517 |
| 2013/0158675 A1 | 6/2013 | Hutchins, III et al. | |
| 2013/0324946 A1 | 12/2013 | Tobias et al. | |
| 2014/0209100 A1 | 7/2014 | Kiser et al. | |
| 2014/0242044 A1 * | 8/2014 | Evans | A61F 2/4618 514/8.8 |
| 2014/0276636 A1 | 9/2014 | Lee et al. | |
| 2015/0080847 A1 | 3/2015 | Cima et al. | |
| 2015/0209277 A1 | 7/2015 | Lee et al. | |
| 2016/0008271 A1 | 1/2016 | Lee | |
| 2016/0199544 A1 | 7/2016 | Lee et al. | |
| 2016/0310715 A1 | 10/2016 | Lee | |

OTHER PUBLICATIONS

Lee et al, "An intravesical device for the sustained delivery of lidocaine to the bladder", Journal of Controlled Release, 2011, vol. 149, No. 2, pp. 133-139.

Tyagi et al, "Urodynamic and Immunohistochemical Evaluation of Intravesical Capsaicin Delivery Using Thermosensitive Hydrogel and Liposomes", Journal of Urology, 2004, vol. 171, No. 1, pp. 483-489.

* cited by examiner

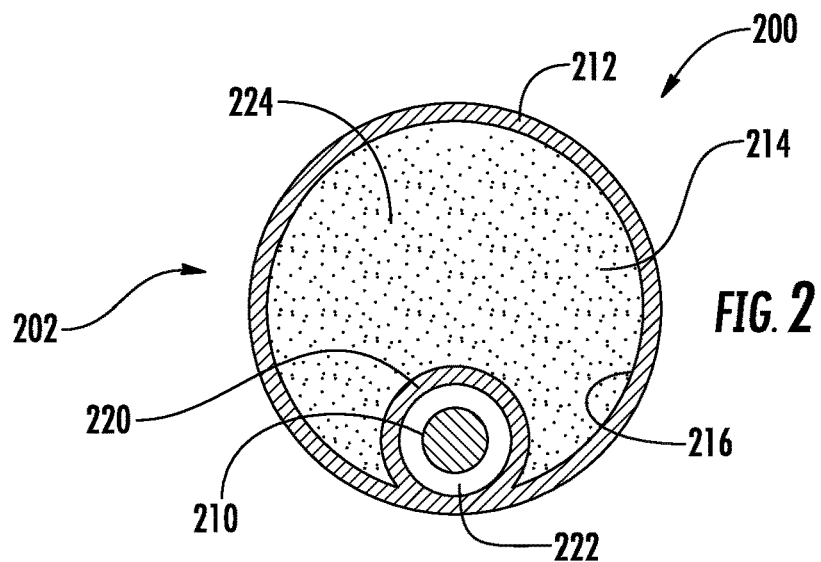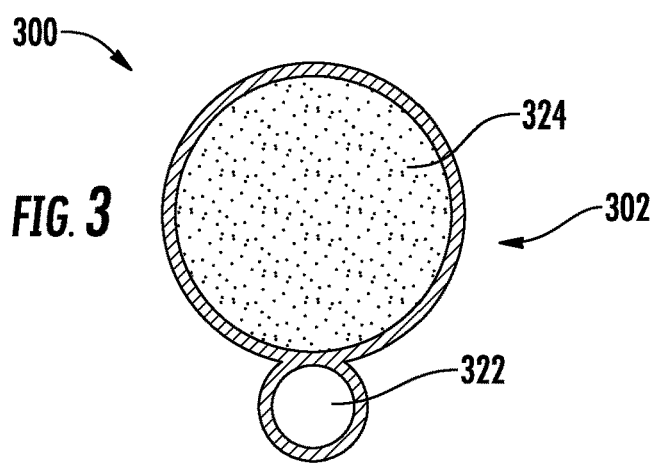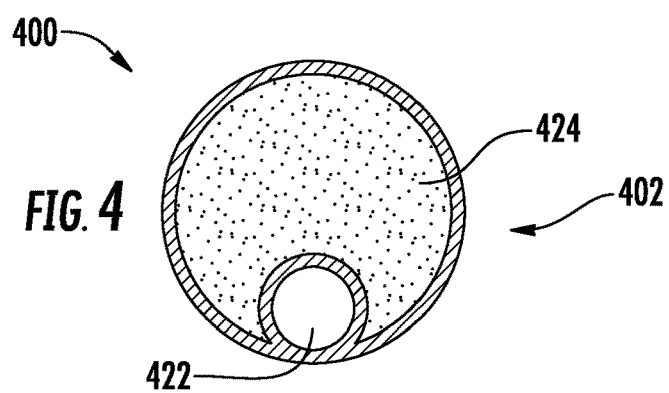

INTRAVESICAL DRUG DELIVERY DEVICES AND METHODS INCLUDING ELASTIC POLYMER-DRUG MATRIX SYSTEMS

CROSS-REFERENCE TO RELATED APPLICATIONS

This application is a divisional of U.S. application Ser. No. 15/321,110, filed Dec. 21, 2016, which is the national stage of PCT/US15/37887, filed Jun. 26, 2015, which claims priority to U.S. Provisional Application No. 62/017,775, filed Jun. 26, 2014, all of which are incorporated by reference herein.

TECHNICAL FIELD

This disclosure is generally in the field of drug delivery devices and more particularly in the field of devices for deployment within a patient, for example in the urinary bladder, for controlled release of drug over an extended period.

BACKGROUND

Devices for local administration of drug to the bladder are known. For example, U.S. Pat. No. 8,679,094 describes intravesical devices for drug delivery that can be inserted into, and effectively and tolerably retained in, the urinary bladder of a patient for controlled release of drug over an extended period. It would be desirable, however, to provide alternative drug delivery device designs, for example to provide suitable release kinetics for different kinds of drugs.

In addition, it would be desirable to provide alternative designs to conventional drug delivery systems to reduce or eliminate potential problems, such as dose dumping, wasting of active pharmaceutical ingredient (API), or other issues that may be associated with the extended, continuous delivery of high potency drugs from devices inserted or implanted into the body of a patient. In particular, it would be desirable to provide a device or system that is relatively easy to manufacture/assemble, and which does not negatively impact the release kinetics of the drug.

Lastly, it would be desirable, in some cases, to provide an elastic intravesical drug delivery device that is capable of maintaining a bladder retention shape without the use of a retention frame element to impart the shape bias characteristics of the device.

SUMMARY

In one aspect, an intravesical drug delivery device is provided which includes an elongated body formed of a matrix system of a drug dispersed in a silicone, wherein the elongated body has a first end, an opposed second end, and an intermediate portion between the first and second ends, and wherein the silicone of the matrix system is cured to bias the elongated body in a coiled retention shape, such that the device is elastically deformable between a relatively straightened shape suited for insertion of the device through a urethra and into the urinary bladder of a patient and the coiled retention shape which is suited to retain the device within the urinary bladder.

In another aspect, an intravesical drug delivery device is provided which includes an elongated body having a first end, an opposed second end, and an intermediate portion between the first and second ends, wherein the elongate body includes (i) a first lumen extending through the intermediate portion in a direction between the first and second ends and which contains a drug, and (ii) a second lumen extending through the intermediate portion in a direction between the first and second ends and which contains a first silicone cured to bias the elongated body in a coiled retention shape, such that the device is elastically deformable between a relatively straightened shape suited for insertion of the device through a urethra and into the urinary bladder of a patient and the coiled retention shape which is suited to retain the device within the urinary bladder. The drug in the first lumen may be in a matrix system in which the drug is dispersed in a second silicone, which may have a lower durometer value than the first silicone.

In still another aspect, an intravesical drug delivery device is provided which includes an elongated body formed of a matrix system of a drug dispersed in a silicone, wherein the elongated body has a first end, an opposed second end, and an intermediate portion between the first and second ends; and an elastic retention frame associated with the elongated body and effective to bias the elongated body into a coiled retention shape. The elastic retention frame may include a nitinol wire or other superelastic wire, which may be disposed within a lumen through the elongated body or within a lumen adjacent to the elongated body.

In yet a further aspect, methods are provided for administering a drug to a patient in need thereof. The methods include inserting into a tissue site within the patient one of the foregoing intravesical drug delivery devices; and then releasing the drug from the device to the tissue site within the patient. The step of inserting may include passing the device through the patient's urethra and into the patient's urinary bladder. For example, the step of inserting may include elastically deforming the device into a relatively straightened shape suitable for passage of the device through the urethra and then permitting the device to elastically deform into the coiled retention shape within the urinary bladder.

In another aspect, methods are provided for making an intravesical drug delivery device. In one embodiment, the method includes providing an elongated, elastic polymeric tube having a first end, an opposed second end, and an intermediate portion between the first and second ends, the intermediate portion comprising an elongated lumen extending between the first and second ends; preparing a fluid matrix system comprising a drug dispersed in a silicone material; injecting the fluid matrix system into the elongated lumen; forming the elongated polymeric tube, with the fluid matrix system therein, into a coiled bladder retention shape; and curing the fluid matrix system into a solid, elastic matrix system to bias the elongated tube in the coiled bladder retention shape, such that an intravesical drug delivery device, which comprises the solid, elastic matrix system, is elastically deformable between a relatively straightened shape suited for insertion of the device through the urethra and the urinary bladder of a patient and the coiled retention shape which is suited to retain the device within the urinary bladder. The silicone of the matrix system may be cured at a temperature from 15° C. to 30° C., optionally using a platinum curing system. The elongated, elastic polymeric tube may further include a second elongated lumen extending between the first and second ends, which optionally may (i) be gas-filled and sealed at its ends to promote buoyancy of the device in the bladder, (ii) contain an elastic retention frame which comprises a nitinol wire or other superelastic wire, or (iii) contain a high durometer silicone without the drug.

In another embodiment, the method for making includes providing a device body which has a drug reservoir and an elongated, elastic polymeric tube which has a first end, an opposed second end, and an intermediate portion between the first and second ends, wherein the intermediate portion comprises first and second elongated lumens extending between the first and second ends; loading a drug into the first elongated lumen; injecting a fluid silicone material into the second elongated lumen; forming the elongated polymeric tube, with the fluid silicone therein, into a coiled bladder retention shape; and curing the fluid silicone material into a solid, elastic silicone material to bias the device body in the coiled bladder retention shape, such that an intravesical drug delivery device, which comprises the device body, is elastically deformable between a relatively straightened shape suited for insertion of the device through the urethra and the urinary bladder of a patient and the coiled retention shape which is suited to retain the device within the urinary bladder. The silicone material may be cured at a temperature from 15° C. to 30° C., optionally using a platinum curing system. The silicone material comprises a high durometer silicone. The drug loaded in the first elongated lumen may be dispersed in a matrix system which includes a second silicone, which may have a lower durometer value than the cured silicone material in the second elongated lumen.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale.

FIG. 2 is a cross-sectional view of another embodiment of a drug delivery device having an elongated body that includes two lumens, with one lumen containing a drug-matrix system.

FIG. 3 is a cross-sectional view of an alternative embodiment of the drug delivery device shown in FIGS. 1A and 1B, without a retention frame.

FIG. 4 is a cross-sectional view of alternative embodiment of the drug delivery device shown in FIG. 2, without a retention frame.

DETAILED DESCRIPTION

The drug delivery devices, which in particular may be configured for intravesical insertion and administration of drug, have been developed that include a silicone-drug matrix system, a high durometer silicone portion biased to provide a coiled retention shape, or a combination thereof. In embodiments, release of the the drug is controlled by diffusion of the drug from the silicone-drug matrix system. These systems advantageously provide alternative designs to conventional drug delivery systems and may reduce or eliminate potential problems, such as dose dumping or wasting of API—which may make the devices particularly well suited for high potency drugs, such as some of those used in the treatment of cancer, for example. Furthermore, in some embodiments, the systems enable an elastic intravesical drug delivery device that is capable of maintaining a bladder retention shape without the use of an elastic wire retention frame element to impart the desired shape bias characteristics of the device.

Drug Delivery Devices

Figure 1A:
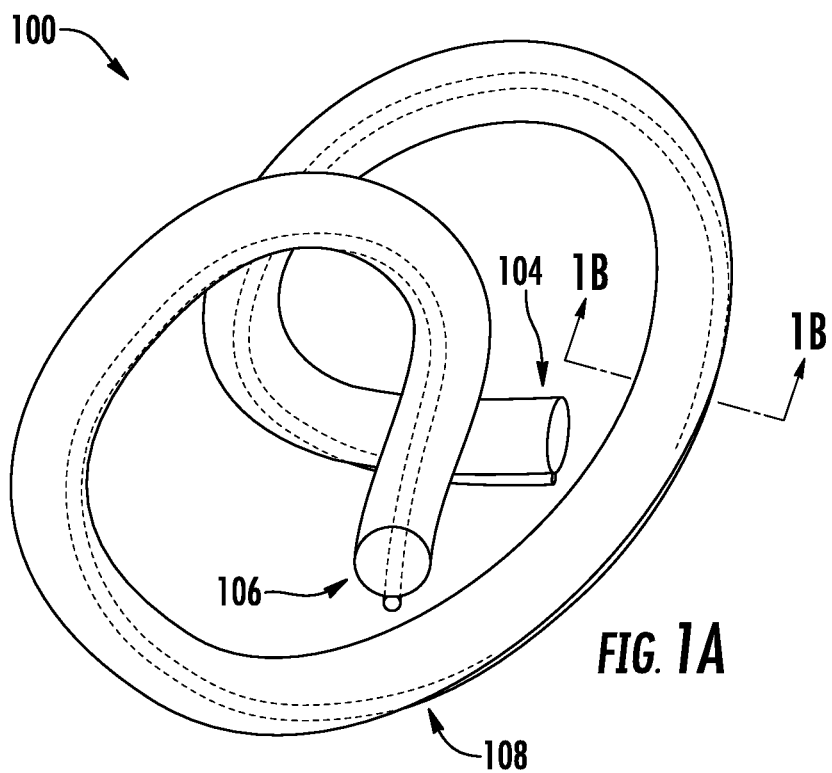
FIG. 1A is a perspective view of one embodiment of a drug delivery device having an elongated body that includes two lumens, with one lumen containing a drug-matrix system.
Figure 1B:
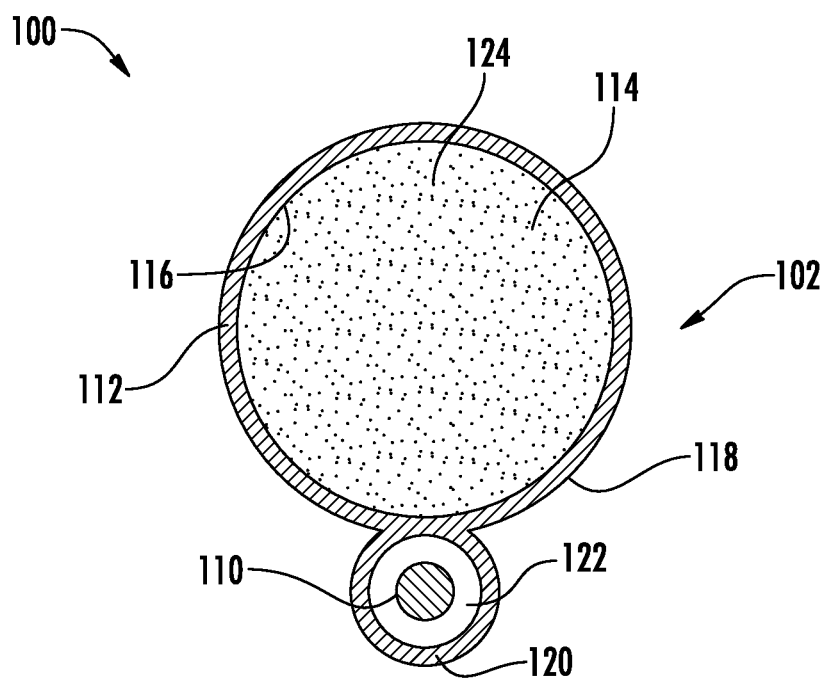
FIG. 1B is a cross-section view of the drug delivery device shown in FIG. 1A, taken along line 1B-1B.

One embodiment of a drug delivery device is shown in FIGS. 1A-1B. The device 100 includes an elongated body 102 having a first end 104, an opposed second end 106, and an intermediate portion 108 that extends between the first and second ends 104, 106. The device 100 further includes an elastic retention frame 110 that is associated with the elongated body 102. The elastic retention frame 110 may be a nitinol wire or other superelastic wire. The retention frames has an overlapping coiled shape in the absence of a compressive load. In other embodiments, the elastic retention frame 110 may be formed of a high durometer silicone.

The elastic retention frame 110 is effective to bias the elongated body 102 into a retention shape, such as the illustrated example "pretzel" shape or another coiled shape suited to retain the device 100 within the bladder or another body cavity. For example, the elastic retention frame 110 may have an elastic limit, modulus, and/or spring constant that allows the device 100 to be introduced into the body cavity in a relatively straightened shape, permits the device 100 to return to the retention shape once inside the body, and impedes the device 100 from assuming the relatively straightened shape within the body in response to expected forces. Such a configuration may limit or prevent accidental expulsion of the device 100 from the body under expected forces. For example, the device 100 may be retained in the bladder during urination or contraction of the detrusor muscle. In a particular embodiment, the drug delivery device 100 is elastically deformable between a relatively straightened shape suitable for insertion of the device through a patient's urethra and into the patient's urinary bladder and a coiled retention shape suited to retain the device within the bladder. The device in this embodiment is sized and shaped to fit through a narrow tubular path of a deployment instrument, such as a catheter or cystoscope.

As used herein, the term "coiled retention shape" generally denotes any shape suited for retaining the device in the intended location within the body, including but not limited to the coiled shape shown in FIG. 1A that is suited for retaining the device, for example, in the bladder. Similarly, the term "relatively straightened shape" generally denotes any shape suited for deploying the drug delivery device into the body. For example, a linear or elongated shape that is suited for deploying the device through the working channel of a catheter, cystoscope, or other deployment instrument positioned in a lumen of the body, such as the urethra. In embodiments, the drug delivery device may naturally assume the retention shape and may be deformed, either manually or with the aid of an external apparatus, into the relatively straightened shape for insertion into the body. Once deployed the device may spontaneously or naturally return to the initial, retention shape for retention in the body.

As shown in FIG. 1B, the elongated body 102 includes a first elastic tubular structure, or tube, 112 that defines a first lumen 114 and a second elastic tubular structure, or tube, 120 that defines a second lumen 122. The first lumen 114 is loaded with a matrix system 124 of a drug dispersed within silicone (or another flexible, biocompatible polymer). The matrix system 124 generally is in direct contact with the inner surface 116 of the tube 112, such that drug from the matrix system diffuses from the matrix system and through the wall of tube 112 in vivo. The second lumen 122, in this embodiment, includes the elastic retention frame 110 located therein. The first and second lumens 114, 122 are longitudinally aligned, with tubes 112 and 120 coupled to each other, or integrally formed together, at a region of the outer surfaces of the tubes, along their lengths. The tubes share a wall structure in this region. The tube 120 may be considered as being connected to the outer surface 118 of tube 112. Other configurations are also envisioned. For example, tube 112 may be attached to tube 120 at discrete points and separate or spaced apart from it at other points.

Another embodiment is illustrated in FIG. 2. Drug delivery device 200 includes an elongated body 202 having a first elastic tubular structure, or tube, 212 that defines a first lumen 214 filled with a matrix system 224 and a second elastic tubular structure, or tube, 220 that defines a second lumen 222. The matrix system 224 includes a drug dispersed within silicone (or another flexible, biocompatible polymer) and generally is in direct contact with the inner surface 216 of the tube 212, such that drug from the matrix system diffuses from the matrix system and through the wall of tube 212 in vivo. The second lumen 222, in this embodiment, includes the elastic retention frame 210 located therein. The first and second lumens 214, 222 are longitudinally aligned, with tubes 212 and 220 coupled to each other, or integrally formed together, at a region of the inner surface 216 of tube 212, and the outer surface of tube 220, along their lengths. The tubes share a wall structure in this region.

Device 200 may have a smaller cross-sectional profile than device 100, since the retention frame and its lumen effectively are located within the same (larger) lumen as the drug matrix system in device 200, whereas the retention frame and its lumen are located outside of the lumen containing the drug matrix system in device 100. The smaller profile may facilitate ease of deployment and retrieval, and therefore may be preferable if the concomitant loss of matrix system volume (and drug payload) is acceptable.

In embodiments, it may be desirable for an intravesical device to possess an elastically deformable, coiled retention shape without the use of an elastic wire, such as one made of nitinol or another superelastic alloy or other material. This can be accomplished in one of several different ways that include curing a silicone (or other biocompatible elastic polymer) while the material is in the desired coiled retention shape, where the cured silicone has sufficient, but not too much, resistance to elastic deformation. In a particular embodiment of an intravesical device, the silicone is selected to have a high durometer value. As used herein, the term "high durometer" means Shore 75 A to Shore 88 A. A high durometer silicone, for example, may be used in the matrix system, if the silicone is compatible with the drug of interest. In embodiments in which the drug is incompatible with the high durometer silicone, then the high durometer silicone can be included in the intravesical device in a region separate from the drug, for example in its own device lumen. In one case, a low durometer silicone may be used in a drug matrix system in one part of the device, while a higher (and high) durometer silicone is provided in a separate part of the device to impart the desired shape retention property.

FIGS. 3 and 4 illustrate device 300 and device 400, respectively, wherein the drug matrix systems 324, 424 are effective themselves to impart the elastic coiled retention shape function of the device 300, 400. The elongated bodies 302, 402, include matrix systems 324, 424, respectively, that are formed of drug and a suitable silicone (or other biocompatible elastic polymeric material) for biasing the devices into a coiled retention shape with a sufficient spring constant, e.g., a high durometer silicone. The lumens 322 and 422 may be used to temporarily house an elastic retention frame during curing of the silicone. In a particularly advantageous embodiment, lumens 322 and 422 are filled with air or another biocompatible gas and then sealed at their ends. The entrapped gas facilitates buoyancy of the device in urine in the bladder, which can aid in retention of the device in the bladder, and possible further promote tolerance, or unnoticeability, of the device by the patient.

The relative advantages and trade-offs of devices 300 and 400 are like those described above for devices 100 and 200. In another embodiment, not shown, the lumens 322 and 422 (and the wall structures defining these lumens) are omitted.

Figure 5:
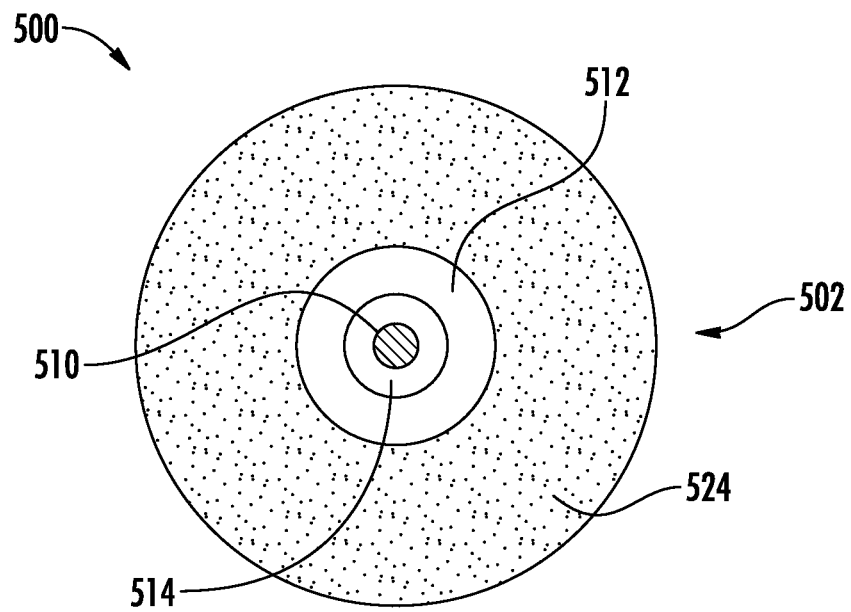
FIG. 5 is a cross-sectional view of one embodiment of a drug delivery device having an elongated body that includes a lumen extending through a drug-matrix system.

Another embodiment of a drug delivery device is shown in FIG. 5. The drug delivery device 500 includes an elongated body 502 formed of a matrix system 524 (e.g., drug dispersed in silicone matrix) and has an elastic annular tube structure 512 that extends through the length of elongated body. The annular tube structure defines a lumen 514 which extends between opposed ends, through an intermediate portion, of the elongated body 502. An elastic retention frame 510, such as a nitinol wire, is disposed in the lumen 514. In an alternative embodiment, the elastic retention frame 510 is replaced with a high durometer silicone cured in a coiled retention shape.

Figure 6:
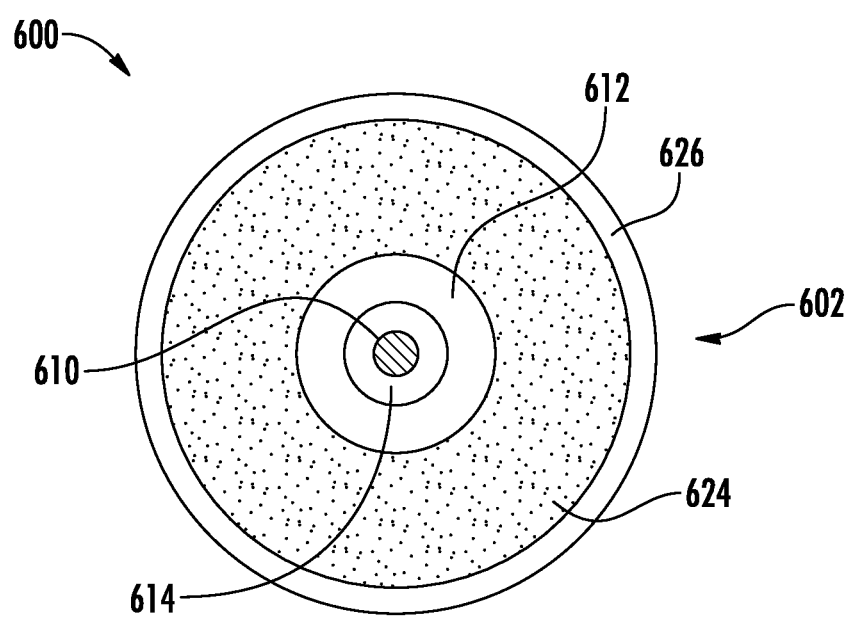
FIG. 6 is a cross-sectional view of another embodiment of a drug delivery device having an elongated body that includes a lumen extending through a drug-matrix system and an outer wall layer disposed about the drug-matrix system.

FIG. 6 illustrates another possible variation of the drug delivery device 500 shown in FIG. 5. The drug delivery device 600 includes an elongated body 602 formed of a matrix system 624 (e.g., drug dispersed in silicone matrix) which has an elastic annular tube structure 612 that extends through the length of elongated body. The annular tube structure defines a lumen 614 which extends between opposed ends, through an intermediate portion, of the elongated body 602. An elastic retention frame 610, such as a nitinol wire, is disposed in the lumen 614. The drug delivery device 600 further includes an outer wall layer 626 that covers at least the intermediate portion of the elongated body 602. The outer wall layer 626 is elastically deformable with the matrix system 624 and may be an annular tube structure, for example formed of silicone, polyurethane, or another water- and drug-permeable elastomeric material. The thickness and composition of the outer wall layer may be selected to facilitate manufacturing of the matrix system, to control release of the drug, or both.

Figure 7:
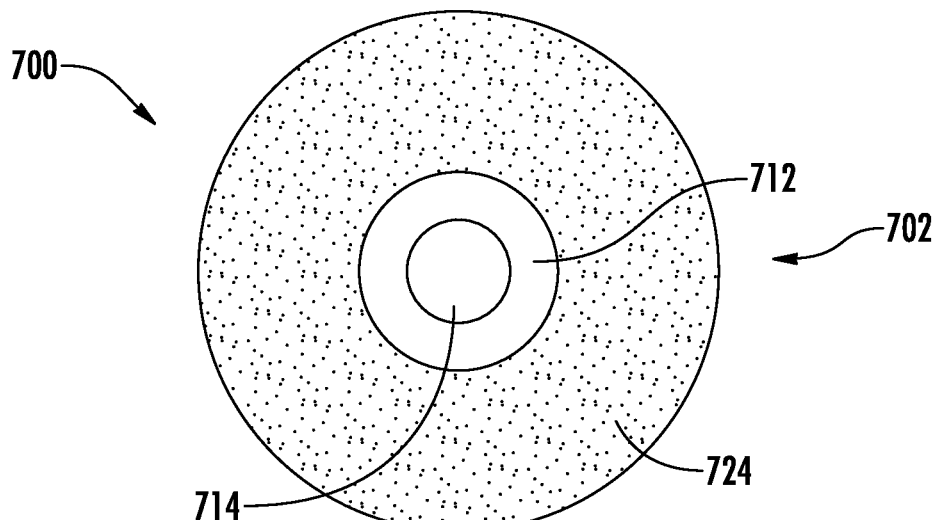
FIG. 7 is a cross-sectional view of an alternative embodiment of the drug delivery device shown in FIG. 5, without a retention frame.

In some embodiments, the elastic retention frame is omitted. Examples of such devices are shown FIGS. 7 and 8. In FIG. 7, drug delivery device 700 includes an elongated body 702 formed of a matrix system 724 (e.g., drug dispersed in silicone matrix) and has an elastic annular tube structure 712 that extends through the length of elongated body. The annular tube structure defines a lumen 714 which extends between opposed ends, through an intermediate portion, of the elongated body 702. Similarly, in FIG. 8, drug delivery device 800 includes an elongated body 802 formed of a matrix system 824 (e.g., drug dispersed in silicone matrix) and has an elastic annular tube structure 812 that extends through the length of elongated body. The annular tube structure defines a lumen 814 which extends between opposed ends, through an intermediate portion, of the elongated body 802. The drug delivery device 800 further includes an outer wall layer 826 that covers at least the intermediate portion of the elongated body 802. The outer wall layer 826 is elastically deformable with the matrix system 824 and may be an annular tube structure, for example formed of silicone, polyurethane, or another water- and drug-permeable elastomeric material.

In these embodiments, the matrix systems 724 and 824 may be formed of drug and a suitable silicone (or other biocompatible elastic polymeric material) for biasing the devices into a coiled retention shape with a sufficient spring constant, e.g., a high durometer silicone. In such cases, the lumens 714 and 814 may be used to temporarily house an elastic retention frame during curing of the silicone. In a particularly advantageous embodiment, lumens 714 and 814 are filled with air or another biocompatible gas and then sealed at their ends. The entrapped gas facilitates buoyancy of the device in urine in the bladder, which can aid in retention of the device in the bladder, and possible further promote tolerance, or unnoticeability, of the device by the patient.

In some embodiments, the selected drug for one reason or another may not be suitable for dispersing in a high durometer silicone. In such cases, it may be desirable to provide a drug delivery device in which the high durometer silicone is in a separate compartment from a compartment containing the drug, which drug may or may not be in a matrix system. Examples of such devices are illustrated in FIGS. 9 and 10.

Figure 9:
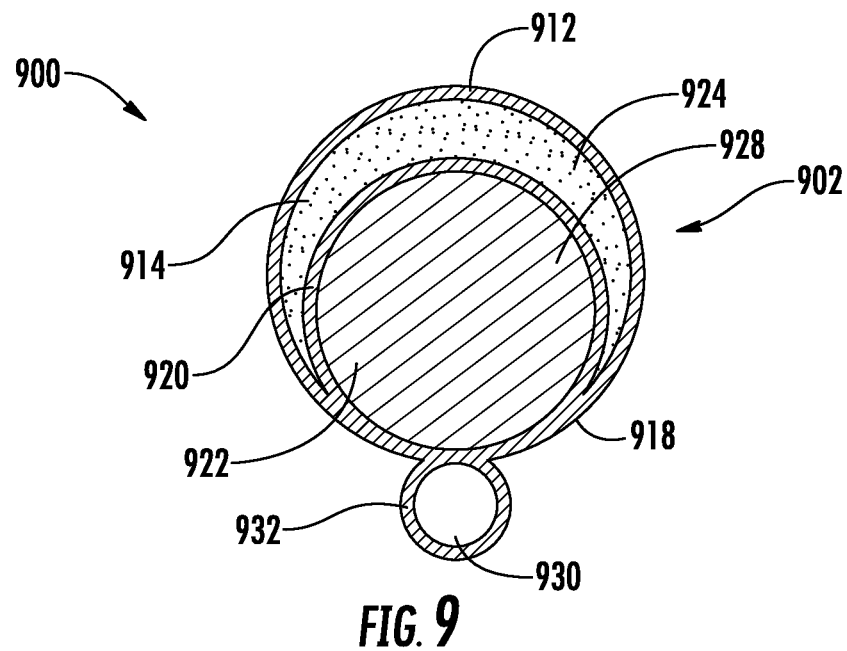
FIG. 9 is a cross-sectional view of one embodiment of a drug delivery device having an elongated body that includes three lumens, wherein a tube defining a smaller lumen extends along an outer surface of a tube defining the largest lumen.

One embodiment of such a drug delivery device is shown in FIG. 9. The drug delivery device 900 has an elongated body 902 that includes three lumens 914, 922, 930 extending in the same direction between the ends of the elongated body. The first lumen 914 is defined in part by a first elastic tubular structure, or tube, 912, and in part by a second elastic tubular structure, or tube, 920. The first lumen 914 is loaded with a matrix system 924 (e.g., drug dispersed in silicone matrix). The second lumen 922 is defined by the second tube 920 and is loaded with a suitable silicone 928 (or other biocompatible elastic polymeric material) for biasing the devices into a coiled retention shape with a sufficient spring constant, e.g., a high durometer silicone. In one embodiment, silicone 928 has a greater durometer value than the matrix material of the matrix system 924. The first and second tubes 912 and 920 are coupled to each other, or integrally formed together, at a region along their lengths. The third lumen 930 is defined in part by a third elastic tubular structure, or tube, 932, which is also coupled to or integrally formed together with tubes 912 and/or 920 at a region along their lengths, connected at a position outside of the annuli of tubes 912 and 920. In the illustrated embodiment, tubes 912, 920, and 932 share a wall structure in the same region. The third lumen 930 may be used to temporarily house an elastic retention frame during curing of the silicone 928. In a particularly advantageous embodiment, lumen 930 is filled with air or another biocompatible gas and then sealed at its ends. The entrapped gas facilitates buoyancy of the device in urine in the bladder, which can aid in retention of the device in the bladder, and possible further promote tolerance, or unnoticeability, of the device by the patient.

Figure 10:
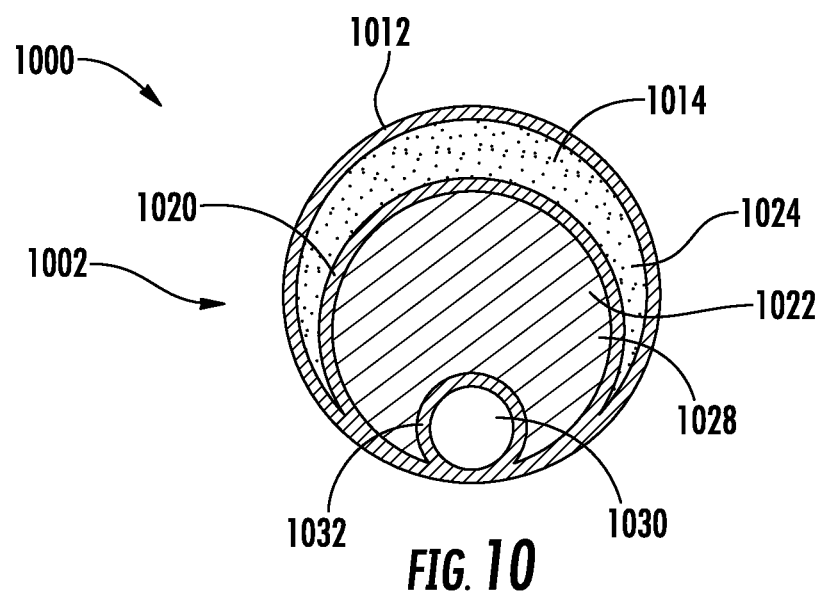
FIG. 10 is a cross-sectional view of a second embodiment of a drug delivery device having an elongated body that includes three lumens, wherein a tube defining a smaller lumen extends along an inner surface (within the annulus) of a tube defining the largest lumen.

FIG. 10 illustrates another embodiment of a drug delivery device having three lumens. The drug delivery device 1000 has an elongated body 1002 that includes three lumens 1014, 1022, 1030 extending in the same direction between the ends of the elongated body. The first lumen 1014 is defined in part by a first elastic tubular structure, or tube, 1022, and in part by a second elastic tubular structure, or tube, 1020. The first lumen 1014 is loaded with a matrix system 1024 (e.g., drug dispersed in silicone matrix). The second lumen 1022 is defined in part by the second tube 1020 and in part by a third tubular structure, or tube, 1032. The second lumen 1022 is loaded with a suitable silicone 1028 (or other biocompatible elastic polymeric material) for biasing the devices into a coiled retention shape with a sufficient spring constant, e.g., a high durometer silicone. In one embodiment, silicone 1028 has a greater durometer value than the matrix material of the matrix system 1024. The first, second, and third tubes 1012, 1020, and 1032 are coupled to each other, or integrally formed together, at one or more regions along their lengths, with tube 1032 connected at a position within the annuli of tubes 1012 and 1020. The third lumen 1030 may be used to temporarily house an elastic retention frame during curing of the silicone 1028. In a particularly advantageous embodiment, lumen 1030 is filled with air or another biocompatible gas and then sealed at its ends. The entrapped gas facilitates buoyancy of the device in urine in the bladder, which can aid in retention of the device in the bladder, and possible further promote tolerance, or unnoticeability, of the device by the patient.

When devices 900 and 1000 are operated in vivo, drug diffuses from the matrix system 924, 1024 and through the wall of tube 912, 1012, which is formed of a water- and drug-permeable elastomeric material.

In an alternative embodiment, the matrix system 924, 1024 is replaced with drug in another form, which may not include a matrix material. For example, the drug may be in a powder form, or in a shaped form, such as a film, which can be inserted into the lumen.

Figure 8:
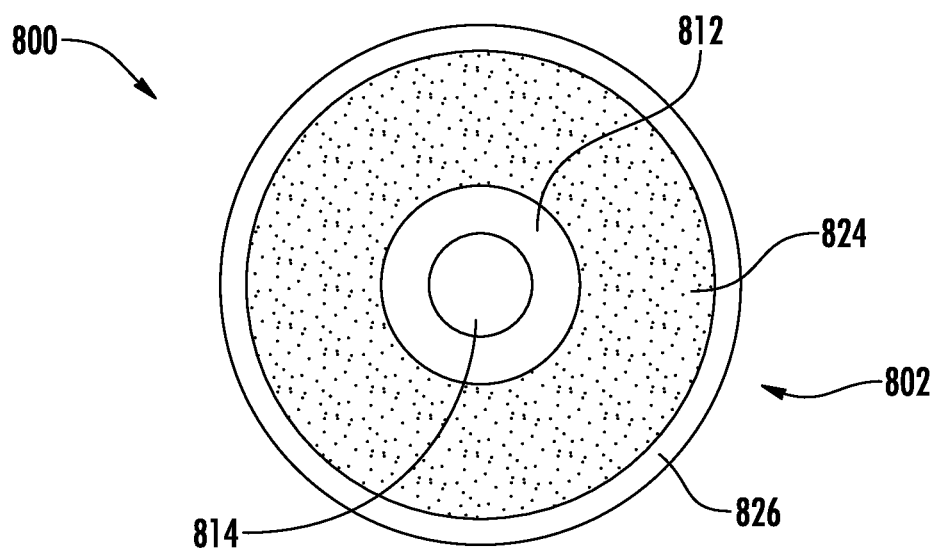
FIG. 8 is a cross-sectional view of an alternative embodiment of the drug delivery device shown in FIG. 6, without a retention frame.
Figure 11:
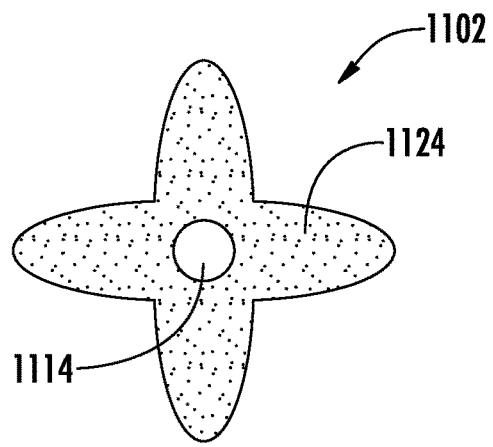
FIG. 11 is a cross-sectional view of an embodiment of an elongated body in the form of a non-cylindrical configuration, as described herein.
Figure 12:
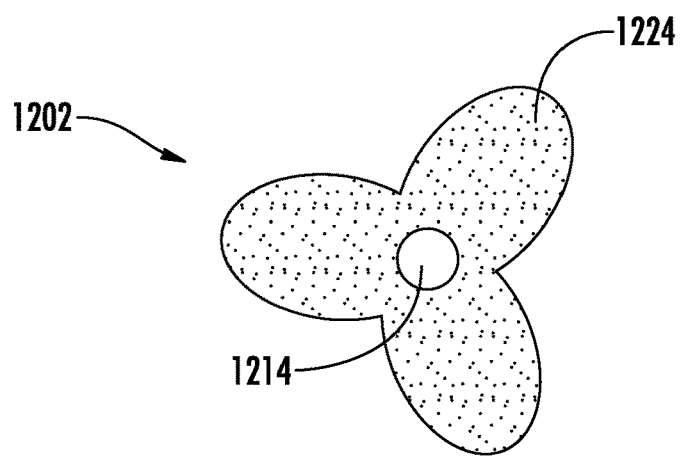
FIG. 12 is a cross-sectional view of another embodiment of an elongated body in the form of a non-cylindrical configuration, as described herein.
Figure 13:
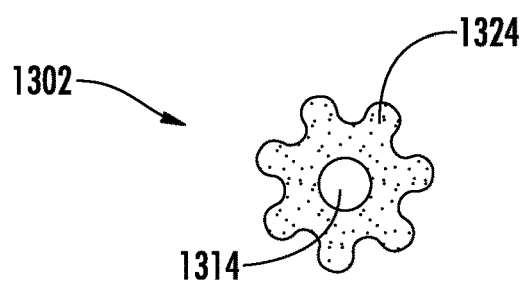
FIG. 13 is a cross-sectional view of yet another embodiment of an elongated body in the form of a non-cylindrical configuration, as described herein.

In operation of the device embodiments shown in FIGS. 5-8, the drug diffuses from the cylindrical surface of the matrix systems (and in the case of the devices of FIGS. 6 and 8, also diffuses through an outer wall layer). With some drugs and matrix systems, it may be desirable to increase the surface area of the matrix system to alter the drug release characteristics. However, the devices, particularly intravesical devices intended to be insertable through the urethra, have overall size limitations. Accordingly, the matrix systems may be designed with increased outer surface area without increasing the maximum cross-sectional dimension. Non-limiting examples of such non-cylindrical elongate bodies are illustrated in FIGS. 11-13. The device 1102 is formed of a matrix system 1124 which include a lumen 1114 that extends between the ends of the elongated body. The device 1202 is formed of a matrix system 1224 which include a lumen 1214 that extends between the ends of the elongated body. The device 1302 is formed of a matrix system 1324 which include a lumen 1314 that extends between the ends of the elongated body. Other shapes are envisioned. The lumen 1114, 1214, 1314 may contain a retention frame, an entrapped gas, or a suitable silicone (or other biocompatible elastic polymeric material) for biasing the devices into a coiled retention shape with a sufficient spring constant, e.g., a high durometer silicone. The devices 1102, 1202, 1302 optionally may further include an outer wall layer (not shown) over the matrix system 1124, 1224, 1324.

The length of the elongated body of the devices described above may be selected depending upon a variety of factors including the specific site of deployment, route of insertion, drug, dosage regimen, and therapeutic application of the device. In one embodiment, the elongated body is from 10 cm to 15 cm in length. In embodiments, the polymeric material used to form the elongated body, at least in part, may be elastic or flexible to permit moving the device between a relatively straightened shape and a retention shape. The elongated body may be formed of elastic material or materials having the necessary modulus or spring constant required to bias the device into a retention shape.

Matrix System

The matrix system includes one or more drugs dispersed in a silicone or other suitable polymeric matrix material. The matrix system may further include or one or more pharmaceutically acceptable excipients known in the art. The amount of drug in the matrix system can vary. In one embodiment, the drug is present in the matrix system in an amount from about 1% to about 20% by weight. For example, it may be between 5% and 20% or between 5% and 15% by weight of the matrix system. Lesser or greater amounts of drug are also possible, depending, for example, on the drug and the polymeric material.

Matrix Material

In a preferred embodiment, the polymeric matrix material is selected to be one that can be mixed with the drug and shape-set (e.g., cured) with no or negligible deleterious effect on the drug. In certain embodiments, the polymeric matrix material is comprises a biocompatible elastomer. Non-limiting examples include silicones and polyurethanes. In a preferred embodiment, the silicone or other matrix material is one that can be cured at or near room temperature, e.g., from about 15° C. to about 30° C. In another embodiment, which may be suitable with some drugs, the silicone or other matrix material is one that can be cured at a temperature from about 15° C. to about 65° C. or less. In a preferred embodiment, the silicone or other matrix material is cured using a platinum curing system, which advantageously does not produce any extractables, compared for example to a peroxide curing system.

In some embodiments, the silicone or other matrix material has a durometer value from 45 Shore A to 88 Shore A. In a preferred embodiment, the silicone or other matrix material has a high durometer value, as defined above.

The matrix material may be bioerodible or non-bioerodible. As used herein, the term "bioerodible" means that the material degrades in-vivo by dissolution, enzymatic hydrolysis, erosion, resorption, or a combination thereof. Examples of non-bioerodible materials include poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly (siloxanes), and copolymers thereof. Examples of bioerodible materials include poly(amides), poly(esters), poly(ester amides), poly(anhydrides), poly(orthoesters), polyphosphazenes, pseudo poly(amino acids), poly(glycerol-sebacate), poly(lactic acids), poly(glycolic acids), poly (lactic-co-glycolic acids), poly(caprolactones), poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis(ε-caprolacton-4-yl) propane to obtain elastomeric properties.

In embodiments where the elongated body includes one or more wall structures, e.g., tubes, the wall structures may be formed from the same or a different elastic polymeric material as the matrix material described above. In embodiments wherein a wall structure is positioned over the drug or matrix system, such that drug release to the patient must pass through the wall structure or a part therefore, then the wall structure preferably is formed of a water- and drug-permeable material. In a preferred embodiment, the wall or walls defining one or more lumens in the elongated body are formed of a silicone.

Drug

The drug can include essentially any therapeutic, prophylactic, or diagnostic agent, such as one that would be useful to deliver locally to the bladder or regionally to another genitourinary tissue site. As used herein, the term "drug" with reference to any specific drug described herein includes its alternative forms, such as salt forms, free acid forms, free base forms, and hydrates. The drug may be a small molecule drug or a biologic. The drug may be a metabolite. Pharmaceutically acceptable excipients known in the art may be included with the drug in the matrix system.

The drug may be dispersed in the biocompatible material in a variety of forms. It may be in powder or granule form, for example. The drug and the polymeric matrix material may be mixed together using any suitable process and equipment known in the art. The drug may be dispersed in the polymeric matrix material homogeneously or heterogeneously.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility.

In one embodiment, the devices provide pain relief to the patient. A variety of anesthetic agents, analgesic agents, and combinations thereof may be used. In embodiments, the device delivers one or more anesthetic agents. The anesthetic agent may be a cocaine analogue. In embodiments, the anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with an anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, and naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

Other intravesical cancer treatments include small molecules, such as Apaziquone, adriamycin, AD-32, doxorubicin, doxetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-α2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In one embodiment, the drug delivery device is used in association with the placement of a ureteral stent, such as to treat pain, urinary urgency or urinary frequency resulting from ureteral stent placement. Non-limiting examples of specific drugs for such treatment include anti-muscarinics, beta-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, anti-muscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutytin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In another embodiment, the drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinc agonist, choline ester).

Elastic Retention Frame

As described above, some embodiments of the drug delivery device include an elastic wire, i.e., an elastic retention frame, to bias the elongated body of the device into a coiled retention shape.

The elastic retention frame is operable to impart elasticity to the device structure, such that the device is elastically deformable between a retention shape and a relatively straightened shape. In one embodiment, the elastic retention frame is biased (i.e., naturally assumes) to have a coiled retention shape, and may be manipulated into the relatively straightened shape for insertion into the body, and then returns to the retention shape upon insertion into the bladder or other body cavity in a patient. The elastic retention frame in the relatively straightened shape may be shaped for insertion into the body through the working channel of a deployment instrument such as a catheter or cystoscope. To achieve this functionality, the elastic retention frame has an elastic limit, modulus, and/or spring constant selected to impede the device from assuming the relatively straightened shape once it is deployed in the patient. Such a configuration may limit or prevent accidental expulsion of the device from the body under expected forces. For example, the device may be retained in the bladder during urination or contraction of the detrusor muscle. Various examples of elastic retention frames are described in U.S. Patent Application Publication 2009/0149833 and U.S. Patent Application Publication 2011/0152839.

The elastic retention frame may be formed of any elastic material effective to impart a suitable modulus or spring constant to the elongated body, and thus to the device. The elastic wire may be formed from a superelastic alloy, such as nitinol or another superelastic alloy.

In embodiments, the elastic retention frame may be in a form having a high enough spring constant to retain the device within a body cavity, such as the bladder. A high modulus material may be used, or a low modulus material. Especially when a low-modulus material is used, the elastic retention frame may have a diameter and/or shape that provide a spring constant without which the frame would significantly deform under the forces of urination. For example, the elastic retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. An elastic retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

Other Device Features

The drug delivery device may also include a retrieval string to facilitate withdrawal of a device from the patient, such as in cases in which the device is non-resorbable or otherwise needs to be removed. For example, the retrieval string may extend (or be selectively extendable) from the patient's urethra to facilitate manual removal of the device residing the patient's bladder.

In one embodiment, the device includes at least one radio-opaque portion or structure to facilitate detection or viewing (e.g., by X-ray imaging or fluoroscopy) of the device by a medical practitioner as part of the implantation, insertion, or retrieval procedure. In one embodiment, the device is constructed, at least in part, of a material that includes a radio-opaque filler material, such as barium sulfate or another radio-opaque material known in the art. Fluoroscopy may be used during deployment and/or retrieval of the device by providing accurate real-time imaging of the position and orientation of the device to the practitioner performing the procedure.

Methods of Making the Device

The devices described herein generally can be made by assembling the drug and polymeric materials, and optionally an elastic retention frame.

In one embodiment, the method includes providing an elongated, elastic polymeric, annular tube which has an elongated lumen extending between the ends of the tube; preparing a fluid matrix system comprising a drug dispersed in a silicone material (or other suitable elastomeric material or precursor); injecting the fluid matrix system into the elongated lumen; forming the elongated polymeric tube, with the fluid matrix system therein, into a coiled bladder retention shape; and curing the fluid matrix system into a solid, elastic matrix system to bias the elongated tube in the coiled bladder retention shape. The annular tube may be silicone, produced by an extrusion process known in the art. The silicone of the matrix system may be cured at a temperature from 15° C. to 30° C., optionally using a platinum curing system known in the art. Other materials and curing systems that may be suitable are also known in the art. The elongated, elastic polymeric tube may further include a second elongated lumen extending through the tube. That second lumen optionally may be filled with a gas (e.g., air) and then sealed at its ends. The second lumen also optionally may be loaded with an elastic retention frame, such as a nitinol wire or other superelastic wire, and then sealed to keep the frame inside the lumen. In another embodiment, the second lumen may be filled with high durometer silicone, without the drug, which is then cured into a solid, elastic form effective to bias the elongated tube in the coiled bladder retention shape, for example when the drug matrix system is not itself so effective.

In some embodiments, an elastic retention frame may be used to hold the shape of the fluid matrix material, the shape of the fluid silicone (without drug), or both, during curing of the matrix material, silicone, or other elastomeric material providing the coiled retention shape. In particular embodiments, the elastic retention frame is temporarily inserted into a separate lumen, i.e., one that does not contain a material undergoing curing. In another embodiment, the shape of the fluid material is maintained during curing by being temporarily held in a mold or other rigid support structure.

In another embodiment, the method for making an intravesical drug delivery device includes providing a device body which has a drug reservoir and an elongated, elastic polymeric tube which has a first end, an opposed second end, and an intermediate portion between the ends, wherein the intermediate portion comprises first and second elongated lumens extending between the first and second ends; loading a drug into the first elongated lumen; injecting a fluid silicone material into the second elongated lumen; forming the elongated polymeric tube, with the fluid silicone therein, into a coiled bladder retention shape; and then curing the fluid silicone material into a solid, elastic silicone material to bias the device body in the coiled bladder retention shape.

The drug may be loaded into the first lumen in a fluidized form or in a solid form. A fluidized form may subsequently be solidified within the first lumen.

Forming an elastic retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the elastic retention frame may be formed by forming the elastic wire into a coiled (e.g., "pretzel") shape and heat treating the elastic wire at a temperature over 500° C. for a period over five minutes. In embodiments in which the elastic retention frame comprises a high modulus elastomer, the step of forming the retention frame may comprising forming one or more windings, coils, loops or spirals in the frame so that the frame functions as a spring. For example, the retention frame may be formed by extrusion, liquid injection molding, transfer molding, or insert molding, among others. Similar techniques may be used to form an elongated body capable of assuming a retention shape without being associated with a retention frame.

Associating the elongated body with the elastic retention frame may include inserting the retention frame into a lumen of the elongated body or fixing the elastic retention from to an outer surface of the elongated body by an adhesive, elastic band, or mechanical fastener.

Some steps or sub-steps of the method of making a drug delivery device may be performed in other orders or simultaneously.

Use and Applications of the Drug Delivery Devices

In embodiments, the drug delivery devices described herein are used to administer one or more drugs to a patient in need thereof. As used herein, the term "patient" refers primarily to a human adult or child, but also may include other suitable mammalian animals, for example in a preclinical trial or in veterinary care. Advantageously, the methods enable the local, continuous delivery of the one or more drugs into the body at therapeutically effective amounts over an extended period.

The device may be implanted, inserted, or deployed at any desired site, including in the urinary bladder or other body cavity or lumen of a patient in need thereof. The drug delivery devices provided herein also may be configured for subcutaneous, intramuscular, intraocular, intraperitoneal, and/or intrauterine implantation. Subsequently, the device may release one or more drugs for the treatment of one or more conditions, locally to one or more tissues at the deployment site and/or regionally to other tissues distal from the deployment site. Thereafter, the device may be retrieved, resorbed, excreted, or some combination thereof.

In one example, the device is inserted into a patient by passing the drug delivery device through a deployment instrument and releasing the device from the deployment instrument into the body. In cases in which the device is inserted into a body cavity such as the bladder, the device assumes a retention shape once the device emerges from the deployment instrument into the cavity.

Once inserted, the device may release the drug, for example by diffusion of the drug from the matrix system. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. In one embodiment, the drug is released continuously over a period from about 1 day to about 30 days in a therapeutically effective amount. The rate of delivery and dosage of the drug can be selected depending upon the drug being delivered and the disease or condition being treated.

In instances where the device is inserted into the bladder, the device may be deployed in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In an embodiment, the device is configured for intravesical insertion for use in the local administration of one or more drugs into the bladder to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

The present invention may be further understood with reference to the following non-limiting examples.

Example 1—Fabrication of Coil Shaped Silicone Device Prototype

Two different device bodies were formed from dual lumen silicone tubes. The tubes each had a large lumen (with an internal diameter of 2.64 mm) and a small lumen (with an internal diameter of 0.51 mm). The tubes each had a wall thickness of 0.2 mm and were elastically deformable. The large lumen of the dual lumen silicone tubes were substantially filled by injection with a silicone: One large lumen with MED-6015 (NuSil, Carpinteria, CA) which has a durometer (hardness) of 50 Shore A, and the other large lumen with MED-4286 (NuSil, Carpinteria, CA) which has a durometer (hardness) of 55 (000) Shore A. The injected silicone was then cured at 37° C. for approximately 3 days with the tubes being maintained in a straight shape. Then a nitinol wire having a bi-oval coiled shape and having a diameter of 0.011 inches (approximately 0.27 mm) was inserted into each small lumen to impart a coiled shape to the silicone tubes.

Example 2—Fabrication of Coil Shaped Silicone Drug Delivery Device

In a prophetic example, the method described in Example 1 would be repeated except that the MED-6015 (NuSil, Carpinteria, CA) and MED-4286 (NuSil, Carpinteria, CA) would each be mixed with a drug to form a fluid matrix system before being injected in to the large lumen of the silicone tubes. The resulting elastic elongate structure comprising a drug matrix system would be suitable as a drug delivery device.

Example 3—Fabrication of Coil Shaped Silicone Device Prototype

Two different device bodies were formed from dual lumen silicone tubes. The tubes each had a large lumen (with an internal diameter of 2.64 mm) and a small lumen (with an internal diameter of 0.51 mm). The tubes each had a wall thickness of 0.2 mm and were elastically deformable. First, a nitinol wire having a bi-oval coiled shape and having a diameter of 0.011 inches (approximately 0.27 mm) was inserted into each small lumen to impart a bi-oval (coiled) shape to the silicone tubes. Then, the large lumen of the dual lumen silicone tubes were substantially filled by injection with a silicone: One large lumen with MED-6015 (NuSil, Carpinteria, CA) and the other large lumen with MED-4286 (NuSil, Carpinteria, CA). The injected silicone was then cured at 37° C. for approximately 3 days with the tubes being in the coiled shape. Each tube filled with cured silicone and a bi-oval shaped nitinol wire (wireform) was observed to possess suitable mechanical characteristics to function as an intravesical device.

Example 4—Fabrication of Silicone Drug Delivery Device Having Adjacent Wireform In a prophetic example, the method described in Example 3 would be repeated except that the MED-6015 (NuSil, Carpinteria, CA) and MED-4286 (NuSil, Carpinteria, CA) would each be mixed with a drug to form a fluid matrix system before being injected into the large lumen of the silicone tubes. The resulting elastic elongate structure comprising a drug matrix system would be suitable as a drug delivery device.

Example 5—Fabrication of Silicone Device Prototype Having Central Wireform

A silicone tube having an internal diameter of 0.020 inches and an outer diameter of 0.037 inches (approximately 0.93 mm) was inserted into the lumen of a sacrificial 9G polytetrafluoroethylene (PTFE) tube (Zeus, Standard Wall Tubing) having internal diameter of 0.118 inches (approximately 2.99 mm) and a wall thickness of 0.020 inches (approximately 0.50 mm). Both ends of the silicone tube extended from the PTFE tube. The annular space in the lumen of the PTFE tube outside of the silicone tube was filled by injection with silicone (MED-6015, NuSil, Carpinteria, CA), which was then cured at 150° C. for 30 minutes or at room temperature for 24 hours. Then the PTFE tube was removed by cutting and peeling, leaving the silicone tube embedded in the body defined by the injected/cured silicone. Then, a bi-oval shape nitinol wireform with a thickness of 0.011 inches (approximately 0.27 mm) was inserted into the silicone tube to impart a coiled shape to the elongated silicone-silicone structure.

Example 6—Fabrication of Silicone Drug Delivery Device Having Adjacent Wireform

In a prophetic example, the method described in Example 5 would be repeated except that the MED-6015 (NuSil, Carpinteria, CA) would be mixed with a drug to form a fluid matrix system before being injected into the annular space in the lumen of the PTFE tube. The resulting elastic elongate structure comprising a drug matrix system would be suitable as a drug delivery device.

Example 7—Fabrication of Shaped Silicone Device Prototype without Wireform

A dual lumen silicone tube having a large lumen internal diameter of 1.52 mm, a small lumen internal diameter of 0.51 mm, and a wall thickness of 0.2 mm was used to build a prototype elastic device. A bi-oval shaped nitinol wire with a thickness of 0.011 inches (approximately 0.27 mm) was first inserted into the small lumen of the dual lumen silicone tube, which imparted a coiled retention shape to the silicone tube. Then, the large lumen of the dual lumen silicone tube was filled by injection with silicone (MED-6019, NuSil, Carpinteria, CA) which has a durometer of 75 Shore A. The injected silicone was then cured at 150° C. for approximately 2 hours in the coiled retention shape. Next, the nitinol wire was removed from the small lumen, leaving the silicone tube in the coiled retention shape, biased by the injected/cured silicone.

This procedure was then repeated with two other dual lumen silicone tubes, each having a different large lumen internal diameter (ID): One with an ID of 2.16 mm and one with an ID of 2.64 mm.

Each tube filled with cured silicone without the nitinol wire (wireform) was observed to possess suitable mechanical characteristics to function as an intravesical device.

Example 8—Fabrication of Silicone Drug Delivery Device without Wireform

In a prophetic example, the method described in Example 7 would be repeated except that the MED-6019 (NuSil, Carpinteria, CA) would be mixed with a drug to form a fluid matrix system before being injected into the large lumen of the silicone tube. The resulting elastic elongate structure comprising a drug matrix system would be suitable as a drug delivery device.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims

We claim:

1. An intravesical drug delivery device comprising:
an elongated body formed of a matrix system of a drug dispersed in a silicone, the elongated body having a first end, an opposed second end, and an intermediate portion between the first and second ends; and
an elastic retention frame associated with the elongated body and effective to bias the elongated body into a coiled retention shape,
wherein the elastic retention frame is disposed within a lumen sealed at its ends and defined by an annular tube which is located within the matrix system, the lumen extending in a direction from the first end to the second end.

2. The device of claim 1, wherein the elastic retention frame comprises a nitinol wire or other superelastic wire.

3. The device of claim 1, further comprising an outer wall layer that covers at least the intermediate portion, wherein the outer wall layer comprises a water- and drug-permeable polymeric material.

4. The device of claim 1, wherein the silicone is a high durometer silicone.

5. The device of claim 1, wherein the drug comprises from 1 wt % to 20 wt % of the matrix system.

6. A method of administering a drug to a patient in need thereof, comprising:
inserting into the patient the intravesical device of claim 1, by passing the device through the patient's urethra and into the patient's urinary bladder; and
releasing the drug from the device to a tissue site within the patient.

7. An intravesical drug delivery device comprising:
an elongated body formed of a matrix system of a drug dispersed in a silicone, the elongated body having a first end, an opposed second end, and an intermediate portion between the first and second ends;
an elastic retention frame associated with the elongated body and effective to bias the elongated body into a coiled retention shape; and
an outer wall layer that covers at least the intermediate portion, wherein the outer wall layer comprises a water- and drug-permeable polymeric material,
wherein the elastic retention frame comprises a nitinol wire or other superelastic wire,
wherein the nitinol wire or other superelastic wire is disposed within a lumen which is adjacent to the elongated body, the lumen extending in a direction from the first end to the second end and being defined by an annular tube which is formed of the water- and drug-permeable polymeric material.

8. An intravesical drug delivery device comprising:
an elongated body formed of a matrix system of a drug dispersed in a biocompatible polymer, the elongated body having a first end, an opposed second end, and an intermediate portion between the first and second ends; and
an elastic retention frame associated with the elongated body and effective to bias the elongated body into a coiled retention shape,
wherein the matrix system extends from the first end to the second end, and
wherein the elastic retention frame is disposed within a lumen sealed at its ends and defined by an annular tube which is located within the matrix system, the lumen extending in a direction from the first end to the second end.

9. The device of claim 8, wherein the biocompatible polymer comprises a polyurethane.

10. An intravesical drug delivery device comprising:
an elongated body formed of a matrix system of a drug dispersed in a non-bioerodible, biocompatible polymer, the elongated body having a first end and an opposed second end wherein the matrix system extends continuously between the first end and the second end, wherein the polymer of the matrix system biases the device in a retention shape, such that the device is elastically deformable between a relatively straightened shape suited for insertion of the device through the urethra and into the urinary bladder of a patient and the retention shape which is suited to retain the device within the urinary bladder.

11. The intravesical drug delivery device of claim 10, wherein the biocompatible polymer comprises a silicone or a polyurethane.

12. The intravesical drug delivery device of claim 10, wherein the drug is present in the matrix system in an amount from 1% to 20% by weight.

13. The intravesical drug delivery device of claim 10, wherein the retention shape is coiled and the elongated body is from 10 cm to 15 cm in length.

14. The intravesical drug delivery device of claim 10, wherein the polymer of the matrix system has a durometer value from 45 Shore A to 88 Shore A.

\* \* \* \* \*